US006864226B1

(12) United States Patent
Coleman et al.

(10) Patent No.: US 6,864,226 B1
(45) Date of Patent: Mar. 8, 2005

(54) ENDOTHELIAL-MONOCYTE ACTIVATING POLYPEPTIDE III

(75) Inventors: Timothy A. Coleman, Gaithersburg, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 407 days.

(21) Appl. No.: 08/972,301

(22) Filed: Nov. 18, 1997

Related U.S. Application Data

(62) Division of application No. 08/483,534, filed on Jun. 7, 1995, now Pat. No. 6,013,483.

(51) Int. Cl.[7] ..................... A61K 38/16; C07K 14/435

(52) U.S. Cl. ............... 514/2; 514/2; 530/300; 530/350

(58) Field of Search ................................ 530/300, 350, 530/351; 514/2, 12; 435/69.1; 424/85.1

(56) References Cited

U.S. PATENT DOCUMENTS

| 5,147,638 A | | 9/1992 | Esman et al. ............... 424/85.8 |
| 5,194,596 A | * | 3/1993 | Tischer et al. |
| 5,350,836 A | * | 9/1994 | Kopchick et al. |
| 5,641,867 A | * | 6/1997 | Stern et al. ............ 530/388.23 |
| 5,885,798 A | | 3/1999 | Bandman et al. |
| 6,090,377 A | | 7/2000 | Bandman et al. |

FOREIGN PATENT DOCUMENTS

| WO | WO 92/15323 | * | 9/1992 |
| WO | WO 9509180 | | 4/1995 |
| WO | WO98/08950 | | 3/1998 |

OTHER PUBLICATIONS

Massague. Cell 49:437–438, May 1987.*
Benjamin et al. Development 125:1591–1598, May 1987.*
Vukicevic et al. PNAS USA 93:9021–9026, Aug. 1996.*
Pilbeam et al. Bone 14:717–720, 1993.*
Kao, J. et al., The Journal of Biological Chem., vol. 267:20239–20247 (1992).
Wakasugi, K., et al., Science, vol. 284:147–151 (1999).
Schwarz, M., et al., Am. J. Physiol, vol. 267:365–75 (1999) (abstract only).
Kleeman, T., et al., The Journal of Biological Chem., vol. 272:14420–11425 (1997).
GeneSeq Accession No.i AAB88409 (Dec. 8, 1997).
Kao et al., J. Biol. Chem., 269(40):25106–25119 (1994).
Kao et al., Behring Inst. M itt., (92):92–106 (1993).
Kao et al., J. Biol. Chem., 267(28):20239–20247 (1992).
Wakasugi et al., "Two distinct cytokines released from a human aminoacyl–tRNA synthetase," Science, Apr. 2, 1999, 284:147–51.

Wilson et al., "Assessing annotation transfer for genomics: quantifying the relations between protein sequence, structure, and function through traditional and probabilistic scores," J. Mol. Biol., Mar. 17, 2000, 297(1):233–49.
Pawlowski et al., "Sensitive sequence comparison as protein function predictor," 2000 Pacific Symposium on BioComputing, p. 1–12.
Wakasugi et al., "Highly differentiated motifs responsible for two cytokine activities of a split human tRNA synthetase," J. Biol. Chem., Aug. 13, 1999, 274:23155–59.
Supplementary Partial European Search Report, Application No. EP95923777.7, Jan. 23, 2001.
Biosis abstract, Accession No. PREV198886058046, Kornelyuk et al., "Tyrosyl transfer RNA synthetase from beef liver purification and physico–chemical properties," *Molekulyarnaya Biologiya* (Moscow), 1988; 22(1):176–86, U.S.S.R.
Biosis abstract, Accession No. PREV19929027274, Ribkinska et al., "An immunochemical approach for studying the structure of tyrosyl–tRNA synthetase from bovine liver," *Biopolimery J Kletka*, 1991, 7(5):33–6, Ukraine.
Wolfson et al., "Purification of mammalian tyrosyl–tRNA synthetase by high–performance liquid chromatography," J. Chromatography, Mar. 9, 1990, 503(1):277–81, The Netherlands.
EMBL Accession No. AF087021, Levanets et al., "Amino acid sequence of bovine tyrosyl–tRNA synthetase. Possible generation of the isolated cytokine–like C–terminal domain via proteolytic cleavage at the 'PEST'–like sequence," Dec. 2, 1998, Ukraine.
GenBank Accession No. H10555, Hillier et al., "ym04e04.r1 Soares infant brain INIB Homo sapiens cDNA clone IMAGE:46655 5' similar to SP:SYM_THETH P23395 Methionyl–TRNA Synthetase, mRNA sequence," Jun. 23, 1995.
GenBank Accession No. AA327316, Adams et al., "EST30628 Colon I Homo sapiens cDNA 5' end, mRNA sequence," Apr. 20, 1997.
GenBank Accession No. H13315, Hillier et al., "yl72b07.r1 Soares infant brain INIB Homo sapiens cDNA clone IMAGE:43366 5' similar to SP:SYYC_Yeast P36421 Tyrosyl–TRNA Synthetase, Cytoplasmic, mRNA sequence," Jun. 27, 1995.
GenBank Accession No. H22113, Hillier et al., "yl34g06.r1 Soares breast 3NbHBst Homo sapiens cDNA clone IMAGE:160186 5', mRNA sequence," Jul. 6, 1995.

* cited by examiner

Primary Examiner—Elizabeth Kemmerer
(74) Attorney, Agent, or Firm—Human Genome Sciences, Inc.

(57) ABSTRACT

A human EMAP III polypeptide and DNA (RNA) encoding such polypeptide and a procedure for producing such polypeptide by recombinant techniques is disclosed. Also disclosed are methods for utilizing such polypeptide for preventing and/or treating neoplasia. Diagnostic assays for identifying mutations in nucleic acid sequence encoding a polypeptide of the present invention and for detecting altered levels of the polypeptide of the present invention for detecting diseases, for example, cancer, are also disclosed.

19 Claims, 3 Drawing Sheets

FIG. 1A

```
1    TACCCCTGCCCTGAAAAAACTGGCCAGGCTGCCTACCCAGATCCCTCAAAGCAGAAGCC

61   AATGGCCAAAGGCCTGCCAAGAATTCAGAACCAGAGGAGGTCATCCCGGCTGGAT
1                                    E  E  V  I  P  S  R  L  D

121  ATCCGTGTGGGGAAAATCATCACTGTGGAGAAGCACCCAGATGCAGACAGCCTGTATGTA
10   I  R  V  G  K  I  I  T  V  E  K  H  P  D  A  D  S  L  Y  V

181  GAGAAGATTGACGTGGGGGAAGCTGAACCACGGACTGTGGTGAGCGGCCTGGTACAGTTC
30   E  K  I  D  V  G  E  A  E  P  R  T  V  V  S  G  L  V  Q  F

241  GTGCCCAAGGAGGAACTGCAGGACAGGCTGGTAGTGGTGCTGTGCAACCTGAAACCCAG
50   V  P  K  E  E  L  Q  D  R  L  V  V  V  L  C  N  L  K  P  Q

301  AAGATGAGAGGAGTCGAGTCCCAAGGCATGCTTCTGTGCTTCTATAGAAGGGATAAAC
70   K  M  R  G  V  E  S  Q  G  M  L  L  C  A  S  I  E  G  I  N

361  CGCCAGGTTGAACCTCTGGACCCTCCGGCAGGCTCTGCTCCTGGTGAGCACGTGTTTGTG
90   R  Q  V  E  P  L  D  P  P  A  G  S  A  P  G  E  H  V  F  V
```

FIG. 1B

```
421  AAGGGCTATGAAAAGGGCCAACCAGATGAGGAGCTCAAGCCCAAGAAGAAAGTCTTCGAG
110   K  G  Y  E  K  G  Q  P  D  E  E  L  K  P  K  K  K  V  F  E

481  AAGTTGCAGGCTGACTTCAAAATTTCTGAGGAGTGCATCGCACAGTGGAAGCAAACCAAC
130   K  L  Q  A  D  F  K  I  S  E  E  C  I  A  Q  W  K  Q  T  N

541  TTCATGACCAAGCTGGGCTCCATTTCCTGTAAATCGCTGAAAGGGGGAACATTAGCTAG
150   F  M  T  K  L  G  S  I  S  C  K  S  L  K  G  G  N  I  S  *

601  CCAGCCCCAGCATCTTCCCCCCTTCTTCCACCACTGA  636
```

FIG. 2

```
130 KGEKKEKKQQSIAGSADSKPIDVSRLDLRIGCIITARKHPDADSLYVEEV 179
            ::|:|::|:|||.  ||||||||::
 32 .........EEVIPSRLDIRVGKIITVEKHPDADSLYVEKI 63

180 DVGEIAPRTVVSGLVNHVPLEQMQNRMVILLCNLKPAKMRGVLSQAMVMC 229
    |||| |||||||||||.  ||  |: |: |||||||| |||| :|:||
 64 DVGEAEPRTVVSGLVQFVPKEELQDRLVVVLCNLKPQKMRGVESQGMLLC 113

230 ASSPE...KIEILAPPNGSVPGDRITFDAF.PGEPDKELNPKKKIWEQIQ 275
    |:.:   .|| ||. .|: |..||:|: |  :|: |:.||||||.:|:
114 ASIEGINRQVEPLDPPAGSAPGEHVFVKGYEKGQPDEELKPKKKVFEKLQ 163

276 PDLHTNDECVATYKGVPFEVKGKGVCRAQTMSNSGIK· 313
    :|:.:||:|: :|: ||.::.|..:  |:
164 ADFKISEECIAQWKQTNFMTKLGSIS.CKSLKGGNIS· 200
```

ENDOTHELIAL-MONOCYTE ACTIVATING POLYPEPTIDE III

This application is a Divisional of and claims priority under 35 U.S.C. § 120 to U.S. application Ser. No. 08/483,534, filed Jun. 7, 1995 (now U.S. Pat. No. 6,013,483, issued on Jan. 11, 2000), which is hereby incorporated herein by reference in its entirety.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as an endothelial-monocyte activating polypeptide III, sometimes hereinafter referred as "EMAP III". The invention also relates to inhibiting the action of such polypeptides.

Immunogenic tumors such as the murine meth A fibrosarcoma, characteristically have a peripheral zone which contains a chronic inflammatory infiltry (Dvorak, H., New Engl. J. Med., 315:1650–1658 (1986)). The presence of these inflammatory cells, often embedded in a mesh work of fibrin which can extend-throughout the tumor stroma, contributes to the concept that tumors might be considered wounds that do not heal (Id.). There have been identified tumor-derived mediators which prime the host response, altering endothelial properties, and attracting inflammatory cells to the tumor. Empa I is a trypsin-sensitive, approximately 40 kda polypeptide distinct from other cytokines and growth factors, and which could activate endothelial cells and monocytes. Another polypeptide has been identified which is the murine homologue of vpf/vegf, a factor which had previously been shown to increase vascular permeability and to be mytogenic for endothelial cells. Recently, another polypeptide has been identified in supernatants of meth A tumor cells (EMAP II). EMAP II activates endothelial cells (ECs) and mononuclear cells potentiating their participation in procoagulant reactions through induction of tissue factor, promoting migration of monocytes and polymorphonuclear leukocytes, and leading to a phlogogenic response when injected into murine foot pads. EMAP II is an apparently unique polypeptide which runs as a broad band.

The polypeptide of the present invention has been putatively identified as a EMAP III as a result of amino acid sequence homology to EMAP II.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, neoplasia such as tumors in cancer.

In accordance with yet a further aspect of the present invention, there are provided antibodies against such polypeptides.

In accordance with another aspect of the present invention, there are provided agonists which mimic EMAP III and bind to the EMAP III receptors to elicit responses.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A and 1B collectively provide an illustration of the cDNA and corresponding deduced amino acid sequence of the polypeptide of the present invention. Sequencing was performed using a 373 automated DNA sequencer (Applied Biosystems, Inc.).

FIG. 2 is an amino acid sequence comparison between the polypeptide of EMAP II on the top line of each comparative row (SEQ ID NO:7) and the polypeptide of EMAP III according to present invention on the bottom line of each comparative row (SEQ ID NO:2).

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 97165 on May 26, 1995.

The ATCC numbers referred to above are directed to biological deposits with the ATCC, 12301 Parklawn Drive, Rockville, Md. 20852. Since the strains referred to are being maintained under the terms of the Budapest Treaty, they will be made available to a patent office signatory to the Budapest Treaty.

The polynucleotide of this invention was discovered in a cDNA library derived from resting T-cells. It contains an open reading frame encoding a protein of 168 amino acid residues. The 168 amino acid sequence represents the active domain of EMAP III which is derived from a prosequence which has been proteolytically cleaved. The protein exhibits the highest degree of homology to EMAP II with 60% identity and 75% similarity over a 150 amino acid stretch. The coding sequence of FIG. 1 (SEQ ID NO:2) illustrates the active domain of the polypeptide and the polypeptide may comprise additional amino acid residues. Although the polypeptide of the present invention is not thought to have a leader sequence, it is a secreted protein.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which, encodes for the mature polypeptide of FIGS. 1A and 1B collectively (SEQ ID NO:2) or for the mature polypeptide encoded by the deposited cDNA may include, but is not limited to: only the coding sequence for the mature polypeptide; the coding sequence for the mature polypeptide and additional coding sequence such as a secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A and 1B collectively (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A and 1B collectively (SEQ ID NO:2) or the same mature polypeptide encoded by the cDNA of the deposited clone as well as variants of such polynucleotides which variants encode for a fragment derivative or analog of the polypeptide of FIGS. 1A and 1B collectively (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A and 1B collectively (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a secretory sequence for controlling transport of a polypeptide from the cell. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A and 1B collectively (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a tide which has the deduced amino acid sequence of FIGS. 1A and 1B collectively (SEQ ID NO:2) or which has the amino acid sequence encoded by the deposited cDNA, as well as fragments, analogs and derivatives of such polypeptide.

The terms "fragment," "derivative" an "analog" when referring to the polypeptide of FIGS. 1A and 1B collectively (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A and 1B collectively (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphènicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The EMAP III polypeptide of the present invention may be employed to regress neoplasia, such as tumors in cancers.

The polynucleotides and polypeptides of the present invention may be employed as research reagents and materials for discovery of treatments and diagnostics to human disease.

This invention provides a method for identification of the receptor for EMAP III. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to EMAP III, and a cDNA library created from this RNA is divided into pools and used to transfect COS cells or other cells that are not responsive to EMAP III. Transfected cells which are grown on glass slides are exposed to labeled EMAP III. EMAP III can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which enhance (agonists) the biological action EMAP III. As an example, a mammalian cell or membrane preparation expressing the EMAP III receptor is incubated with a labelled compound. The ability of the compound to bind to the EMAP III receptor is then measured. The ability to bind to the receptors is measured by the response of a known second messenger system following interaction of the cmpound and the receiptor. Such second messenger systems include but are not limited to cAMP guanylate cyclase, ion channels or phosphoinositide hydrolysis.

The polypeptides and agonists of the present invention may be employed in combination with a suitable pharmaceutical carrier. Such compositions comprise a therapeutically effective amount of the polypeptide or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or agonists of the present invention may be employed in conjunction with other therapeutic compounds.

The pharmaceutical compositions may be administered in a convenient manner such as by the oral, direct injection, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The EMAP III polypeptides and agonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and $\beta$-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the $\beta$-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, $\psi$-2, $\psi$-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of EMAP III.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding EMAP III can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and SI protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of EMAP III Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the EMAP III antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled EMAP III and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of EMAP III

The DNA sequence encoding EMAP III, ATCC #97165, is initially amplified using PCR oligonucleotide primers corresponding to the 5' sequences of the processed EMAP III protein (minus the signal peptide sequence) and the vector sequences 3' to the EMAP III gene. Additional nucleotides corresponding to EMAP III were added to the 5' and 3' sequences respectively. The 5' oligonucleotide primer has the sequence 5' GATCGGATCCGAGGAGGTCATC-CCATCC 3' (SEQ ID NO:3) contains a BamHI restriction enzyme site followed by EMAP III coding sequence starting from the initial amino acid (Glu) of the processed protein. The 3' sequence 5' GATCAAGCTTC TAGATAATGTTC-CCCCC 3' (SEQ ID NO:4) contains complementary sequences to HindIII and is followed by nucleotides of EMAP III coding sequence starting from the terminal amino acid. The restriction enzyme sites correspond to the restriction enzyme sites on the bacterial expression vector pQE-9 (Qiagen, Inc., Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and HindIII. The amplified sequences were ligated into pQE-9 and were inserted in frame with the sequence encoding for the histidine tag and the RBS. The ligation mixture was then used to transform *E. coli* strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized EMAP III was purified from this solution by chromatography on a Nickel-Chelate column under conditions that allow for tight binding by proteins containing the 6-His tag (Hochuli, E. et al., J. Chromatography 411:177–184 (1984)). EMAP III protein (>90% pure) was eluted from the column at pH 5.0 and was pooled and dialyzed versus decreasing concentrations of GnHCl, and then finally into a buffer containing 20 mM Tris HCl pH 8.0; 59 mM NaCl; 0.1% w/v octyl-β-glucoside. The concentration of soluble protein was determined using a BioRad protein assay, and bacterial LPS contamination assayed.

EXAMPLE 2
Cloning and Expression of EMAP III Using the Baculovirus Expression System The DNA sequence encoding the full length EMAP III protein, ATCC #97165, is amplified using PCR oligonucleotide primers corresponding to the 5' and 3' sequences of the gene:

The 5' primer has the sequence 5' GATCGGATCCGAG-GAGGTCATCCCATCC 3' (SEQ ID NO:5) and contains a BamHI restriction enzyme site (in bold) the first 18 nucleotides of the EMAP III gene.

The 3' primer has the sequence 5' GATCGGATCCCTA GATAATGTTCCCCCC 3' (SEQ ID NO:6) and contains the cleavage site for the restriction endonuclease BamHI and 18 nucleotides complementary to the 3' sequence of the EMAP III gene. The amplified sequences are isolated from a 1% agarose gel using a commercially available kit ("Geneclean," BIO 101 Inc., La Jolla, Calif.). The fragment is then digested with the endonuclease BamHI and purified again on a 1% agarose gel. This fragment is designated F2.

The vector pRG1 (modification of pVL941 vector, discussed below) is used for the expression of the EMAP III protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonuclease BamHI. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzyme BamHI and dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac EMAP III) with the EMAP III gene using the enzyme BamHI. The sequence of the cloned fragment is confirmed by DNA sequencing.

5 μg of the plasmid pBac EMAP III is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac EMAP III are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-EMAP III at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant EMAP III in COS Cells

The expression of plasmid, EMAP III HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, an SV40 intron and polyadenylation site. A DNA fragment encoding the entire EMAP III precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding EMAP III, ATCC #97165, is constructed by PCR using two primes: the 5' primer 5' GATCGGATCCGAGGAGGTCATCCCATCC 3' (SEQ ID NO:5) contains a BamHI site followed by 18 nucleotides of EMAP III coding sequence starting from the initiation codon; the 3' sequence 5' GATCAAGCTTCTAGATAATGT-TCCCCCC 3' (SEQ ID NO:6) contains complementary sequences to a BamHI site, translation stop codon, HA tag and the last 18 nucleotides of the EMAP III coding sequence. Therefore, the PCR product contains a BamHI site, EMAP III coding sequence followed by HA tag fused in frame, and a translation termination stop codon next to the HA tag. The PCR amplified DNA fragment and the vector, pcDNAI/Amp, are digested with BamHI restriction enzyme and ligated. The ligation mixture is transformed into *E. coli* strain SURE (Stratagene Cloning Systems, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant EMAP III, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the EMAP III HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated protein comprising amino acid residues 1 to 168 of SEQ ID NO:2.

2. The isolated protein of claim 1 wherein the amino acid sequence further comprises a heterologous polypeptide.

3. The protein of claim 1 wherein said isolated protein is glycosylated.

4. The protein of claim 1 wherein said isolated protein is fused to polyethylene glycol.

5. A protein produced by a method comprising:
 (a) expressing the protein of claim 1 by a cell; and
 (b) recovering the protein.

6. A composition comprising the isolated protein of claim 1 and a pharmaceutically acceptable carrier.

7. An isolated protein comprising an amino acid sequence selected from the group consisting of:
 (a) an amino acid sequence of the full-length polypeptide encoded by the cDNA in ATCC Deposit No. 97165;
 (b) an amino acid sequence of the full-length polypeptide, excluding the N-terminal methionine residue, encoded by the cDNA in ATCC Deposit No. 97165; and
 (c) an amino acid sequence of the mature polypeptide encoded by the cDNA in ATCC Deposit No. 97165.

8. The protein of claim 7 which comprises amino acid sequence (a).

9. The protein of claim 7 which comprises amino acid sequence (b).

10. The protein of claim 7 which comprises amino acid sequence (c).

11. The protein of claim 7 wherein the amino acid sequence further comprises a heterologous polypeptide.

12. The protein of claim 7 wherein said isolated protein is glycosylated.

13. The protein of claim 7 wherein said isolated protein is fused to polyethylene glycol.

14. A protein produced by a method comprising:
 (a) expressing the protein of claim 7 by a cell; and
 (b) recovering the protein.

15. A composition comprising the isolated protein of claim 7 and a pharmaceutically acceptable carrier.

16. A substantially purified polypeptide comprising the amino acid sequence of SEQ ID NO:2.

17. A pharmaceutical composition comprising the amino acid sequence of SEQ ID NO:2 and a pharmaceutically acceptable excipient.

18. The isolated protein of claim 1 wherein said protein consists of amino acid residues 1 to 168 of SEQ ID NO:2.

19. The isolated protein of claim 7 wherein said protein consists of an amino acid sequence of the mature polypeptide encoded by the cDNA in ATCC Deposit No. 97165.

* * * * *

UNITED STATES PATENT AND TRADEMARK OFFICE
CERTIFICATE OF CORRECTION

PATENT NO.    : 6,864,226 B1
DATED         : March 8, 2005
INVENTOR(S)   : Timothy A. Coleman et al.

It is certified that error appears in the above-identified patent and that said Letters Patent is hereby corrected as shown below:

Title page,
Item [*] Notice, "Subject to any disclaimer, the term of this patent is extended or adjusted under 35 U.S.C. 154 (b) by 407 days"; should read -- Subject to any disclaimer, the term of this patent is extended or adjusted under 35 U.S.C. 154(b) 0 days. --.

Signed and Sealed this

Twenty-fourth Day of January, 2006

JON W. DUDAS
*Director of the United States Patent and Trademark Office*

SEQUENCE LISTING

<160> NUMBER OF SEQ ID NOS: 7

<210> SEQ ID NO 1
<211> LENGTH: 636
<212> TYPE: DNA
<213> ORGANISM: Homo sapiens
<220> FEATURE:
<221> NAME/KEY: CDS
<222> LOCATION: (94)..(600)

<400> SEQUENCE: 1

```
tacccctgcc ctgaaaaaac tggccagcgc tgcctaccca gatccctcaa agcagaagcc      60
aatggccaaa ggcctgccaa gaattcagaa cca gag gag gtc atc cca tcc cgg     114
                                   Glu Glu Val Ile Pro Ser Arg
                                     1               5 ctg gat atc cgt gtg ggg aaa atc atc act gtg gag aag cac cca gat      162
Leu Asp Ile Arg Val Gly Lys Ile Ile Thr Val Glu Lys His Pro Asp
         10                  15                  20 gca gac agc ctg tat gta gag aag att gac gtg ggg gaa gct gaa cca      210
Ala Asp Ser Leu Tyr Val Glu Lys Ile Asp Val Gly Glu Ala Glu Pro
 25                  30                  35 cgg act gtg gtg agc ggc ctg gta cag ttc gtg ccc aag gag gaa ctg      258
Arg Thr Val Val Ser Gly Leu Val Gln Phe Val Pro Lys Glu Glu Leu
 40                  45                  50                  55 cag gac agg ctg gta gtg gtg ctg tgc aac ctg aaa ccc cag aag atg      306
Gln Asp Arg Leu Val Val Val Leu Cys Asn Leu Lys Pro Gln Lys Met
                 60                  65                  70 aga gga gtc gag tcc caa ggc atg ctt ctg tgt gct tct ata gaa ggg      354
Arg Gly Val Glu Ser Gln Gly Met Leu Leu Cys Ala Ser Ile Glu Gly
             75                  80                  85 ata aac cgc cag gtt gaa cct ctg gac cct ccg gca ggc tct gct cct      402
Ile Asn Arg Gln Val Glu Pro Leu Asp Pro Pro Ala Gly Ser Ala Pro
         90                  95                 100 ggt gag cac gtg ttt gtg aag ggc tat gaa aag gga caa cca gat gag      450
Gly Glu His Val Phe Val Lys Gly Tyr Glu Lys Gly Gln Pro Asp Glu
    105                 110                 115 gag ctc aag ccc aag aag aaa gtc ttc gag aag ttg cag gct gac ttc      498
Glu Leu Lys Pro Lys Lys Lys Val Phe Glu Lys Leu Gln Ala Asp Phe
120                 125                 130                 135 aaa att tct gag gag tgc atc gca cag tgg aag caa acc aac ttc atg      546
Lys Ile Ser Glu Glu Cys Ile Ala Gln Trp Lys Gln Thr Asn Phe Met
                140                 145                 150 acc aag ctg ggc tcc att tcc tgt aaa tcg ctg aaa ggg ggg aac att      594
Thr Lys Leu Gly Ser Ile Ser Cys Lys Ser Leu Lys Gly Gly Asn Ile
            155                 160                 165 agc tagccagccc agcatcttcc cccttcttc caccactga                        636
Ser
```

<210> SEQ ID NO 2
<211> LENGTH: 168
<212> TYPE: PRT
<213> ORGANISM: Homo sapiens

<400> SEQUENCE: 2

```
Glu Glu Val Ile Pro Ser Arg Leu Asp Ile Arg Val Gly Lys Ile Ile
  1               5                  10                  15

Thr Val Glu Lys His Pro Asp Ala Asp Ser Leu Tyr Val Glu Lys Ile
             20                  25                  30

Asp Val Gly Glu Ala Glu Pro Arg Thr Val Val Ser Gly Leu Val Gln
```

```
              35                  40                  45
    Phe Val Pro Lys Glu Glu Leu Gln Asp Arg Leu Val Val Leu Cys
     50                  55                  60

Asn Leu Lys Pro Gln Lys Met Arg Gly Val Glu Ser Gln Gly Met Leu
 65                  70                  75                  80

Leu Cys Ala Ser Ile Glu Gly Ile Asn Arg Gln Val Glu Pro Leu Asp
             85                  90                  95

Pro Pro Ala Gly Ser Ala Pro Gly Glu His Val Phe Val Lys Gly Tyr
            100                 105                 110

Glu Lys Gly Gln Pro Asp Glu Glu Leu Lys Pro Lys Lys Val Phe
            115                 120                 125

Glu Lys Leu Gln Ala Asp Phe Lys Ile Ser Glu Glu Cys Ile Ala Gln
    130                 135                 140

Trp Lys Gln Thr Asn Phe Met Thr Lys Leu Gly Ser Ile Ser Cys Lys
145                 150                 155                 160

Ser Leu Lys Gly Gly Asn Ile Ser
                165

<210> SEQ ID NO 3
<211> LENGTH: 28
<212> TYPE: DNA
<213> ORGANISM: Artificial Sequence
<220> FEATURE:
<223> OTHER INFORMATION: Contains a BamHI restriction enzyme site.

<400> SEQUENCE: 3
gatcggatcc gaggaggtca tcccatcc                                      28

<210> SEQ ID NO 4
<211> LENGTH: 28
<212> TYPE: DNA
<213> ORGANISM: Artificial Sequence
<220> FEATURE:
<223> OTHER INFORMATION: Contains complementary sequences to HindIII.

<400> SEQUENCE: 4
gatcaagctt ctagataatg ttccccccc                                     28

<210> SEQ ID NO 5
<211> LENGTH: 28
<212> TYPE: DNA
<213> ORGANISM: Artificial Sequence
<220> FEATURE:
<223> OTHER INFORMATION: Contains a BamHI restriction enzyme site.

<400> SEQUENCE: 5
gatcggatcc gaggaggtca tcccatcc                                      28

<210> SEQ ID NO 6
<211> LENGTH: 28
<212> TYPE: DNA
<213> ORGANISM: Artificial Sequence
<220> FEATURE:
<223> OTHER INFORMATION: Contains the cleavage site for the restriction
      endonuclease BamHI

<400> SEQUENCE: 6
gatcggatcc ctagataatg ttccccccc                                     28

<210> SEQ ID NO 7
<211> LENGTH: 183
<212> TYPE: PRT
```

-continued

```
<213> ORGANISM: Homo sapiens

<400> SEQUENCE: 7

Lys Gly Glu Lys Lys Glu Lys Lys Gln Gln Ser Ile Ala Gly Ser Ala
1               5                   10                  15

Asp Ser Lys Pro Ile Asp Val Ser Arg Leu Asp Leu Arg Ile Gly Cys
            20                  25                  30

Ile Ile Thr Ala Arg Lys His Pro Asp Ala Asp Ser Leu Tyr Val Glu
        35                  40                  45

Glu Val Asp Val Gly Glu Ile Ala Pro Arg Thr Val Val Ser Gly Leu
    50                  55                  60

Val Asn His Val Pro Leu Glu Gln Met Gln Asn Arg Met Val Ile Leu
65                  70                  75                  80

Leu Cys Asn Leu Lys Pro Ala Lys Met Arg Gly Val Leu Ser Gln Ala
                85                  90                  95

Met Val Met Cys Ala Ser Ser Pro Glu Lys Ile Glu Ile Leu Ala Pro
                100                 105                 110

Pro Asn Gly Ser Val Pro Gly Asp Arg Ile Thr Phe Asp Ala Phe Pro
            115                 120                 125

Gly Glu Pro Asp Lys Glu Leu Asn Pro Lys Lys Lys Ile Trp Glu Gln
        130                 135                 140

Ile Gln Pro Asp Leu His Thr Asn Asp Glu Cys Val Ala Thr Tyr Lys
145                 150                 155                 160

Gly Val Pro Phe Glu Val Lys Gly Lys Gly Val Cys Arg Ala Gln Thr
                165                 170                 175

Met Ser Asn Ser Gly Ile Lys
                180
```